United States Patent

Musich

[11] Patent Number: 5,964,589
[45] Date of Patent: Oct. 12, 1999

[54] ORTHODONTIC ARCH STABILIZATION DEVICE AND METHOD

[76] Inventor: David R. Musich, 1449 Thor Dr., Inverness, Ill. 60067

[21] Appl. No.: 09/035,253

[22] Filed: Mar. 5, 1998

[51] Int. Cl.[6] ..................................................... A61C 3/00
[52] U.S. Cl. ................................................................ 433/20
[58] Field of Search ............................................... 433/20

[56] References Cited

U.S. PATENT DOCUMENTS

| | | |
|---|---|---|
| 2,406,527 | 8/1946 | Berke .................................... 433/20 |
| 3,123,913 | 3/1964 | Rubin . |
| 3,618,214 | 11/1971 | Armstrong . |
| 3,987,547 | 10/1976 | Moss . |
| 3,988,832 | 11/1976 | Wallshein ............................. 433/20 |
| 3,997,970 | 12/1976 | Hodgson . |
| 4,708,646 | 11/1987 | Jasper . |
| 5,018,969 | 5/1991 | Andreiko et al. . |
| 5,080,584 | 1/1992 | Karabin . |
| 5,317,074 | 5/1994 | Hammar et al. . |
| 5,344,315 | 9/1994 | Hanson . |

FOREIGN PATENT DOCUMENTS

| | | | |
|---|---|---|---|
| 91/03212 | 3/1991 | WIPO ................................. | 433/20 |

OTHER PUBLICATIONS

Bearn, David R., "Bonded Orthodontic Retainers: A Review", Am. Journal of Orthodontic Dentofac. Orthop., Aug. 1995 (207–213).

Lubit, Erwin C., "The Bonded Lingual Retainer," J. Clin. Orthod., May 1979 (311–313).

Diamond, Michael, "Resin Fiberglass Bonded Retainer", J. Clin. Orthod., Mar. 1987 (182–183).

Jager, A. and Radlanski, R.J., "Technique Clinic Bonded Lingual Anchorage Appliance", J. Clin. Orthod., Aug. 1989 (550—550).

Westbrook, Jr., Robert E. and Doleac, Jr., Philbert C., "Technical Clinic Simplified Placement of Bonded 3—3 Retainers," J. Clin. Orthod., Jan. 1989 (34–35).

Orchin, Jeremy D., "Permanent Lingual Bonded Retainer," J. Clin. Orthod., Apr. 1990 (229–231).

Lew, Kenneth K. K., "Direct–Bonded Lingual Retainer," J. Clin. Orthod., Jul. 1989 (490–491).

Axellson, Stefan and Zachrisson, Bjorn, "Clinical Experience with Direct–Bonded Labial Retainers," J. Clin. Orthod., Aug. 1992 (480–490).

Chen, Richard S., "Prefabricated Bonded Mandibular Retainer," J. Clin. Orthod., Nov. 1978 (788–789).

Primary Examiner—Todd E. Manahan
Attorney, Agent, or Firm—Welsh & Katz., Ltd.

[57] ABSTRACT

An orthodontic arch stabilization device comprises a plurality of links connected to form an elongated chain is secured through selected links directly or through bracket bases to a patient's teeth which are to be stabilized. The links can be rigid and of metal, such as stainless steel or a noble metal. A method of stabilizing teeth employs the arch stabilization device and includes preparing the lingual surfaces of the teeth to be stabilized, applying adhesive to the lingual surfaces of the teeth, placing the device in passive contact with the adhesive on the lingual surfaces, and at least partially curing the adhesive.

19 Claims, 2 Drawing Sheets

ORTHODONTIC ARCH STABILIZATION DEVICE AND METHOD

BACKGROUND OF THE INVENTION

1. Field of the Invention

The present invention relates to the stabilization of teeth primarily following orthodontic movement of the teeth. Additionally, the stabilization device may be used following dental trauma which requires tooth immobilization for healing, and to stabilize mobile teeth that have had significant bone loss secondary to periodontal disease.

2. Description of Related Art

Dental arch stabilization following corrective orthodontic tooth movement, healing from traumatic tooth displacement, and stabilization of mobile teeth affected by periodontal disease currently employ one or more bonded wires, which may be a single strand of large gauge wire, a multistrand wire, or strands of fiberglass cemented (bonded) directly or secured to stainless steel bases that are affixed to selected teeth of a patient.

An example of the proposed use of multi-strand arch wires is described in U.S. Pat. No. 5,344,315; in U.S. Pat. Nos. 3,618,214 and 3,997,970 wherein a coiled spring is described. However, coiled springs are most commonly used for purposes of tooth movement rather than tooth stabilization.

However, while these and other attempted improvements in arch stabilization devices have advanced the art, each have disadvantages. The primary objection to these devices is the propensity, after initial installation and adjustment, to their being deformed or broken by normal mastication, particularly of hard objects, such as bones, nuts, crusts, ice and other objects, or upon being accidentally struck, such as in a fall or by a blow to the mouth of the patient. Unintended and undesirable deformation or breaking of the arch stabilization device often causes discomfort to the patient and requires adjustment or replacement of the device in order for proper stabilization to continue. Therefore, there is a need for dental arch stabilization devices which have improved resistance to more than momentary deformation, while maintaining the corrected tooth positions.

SUMMARY OF THE INVENTION

Hence, it is one object of the present invention to provide an improved mechanism for dental arch stabilization used for the retention phase of orthodontic treatment and for stabilization of loose teeth caused by trauma and/or caused by bone loss associated with periodontal disease.

It is another object of the present invention to provide improved arch stabilization devices which resist deformation and breakage while in use in the mouth following installation and adjustment.

It is still another object of the present invention to provide an improved method for stabilizing teeth in a patient.

These and other objects and advantages of the present invention will be apparent from the following description considered in conjunction with the accompanying drawings.

In accordance with the present invention an improved arch stabilization device is provided wherein a plurality of links are connected to form an elongated chain which is adapted to have selected links thereof secured to selected teeth of a patient to be treated. The improved device of this invention is particularly useful when secured to a surface of selected teeth to maintain the arch form and to reduce the tendency of teeth to return to their former positions following repositioning by orthodontic procedures.

Preferably the plurality of links of the device of the present invention are each rigid, and most preferably are formed of metal, while the elongated chain formed of the links is relatively flexible due to its structure when impacted by forces at an angle or transverse to its longitudinal direction of elongation. The plurality of links may preferably be formed of stainless steel of the same composition and nature of stainless steel wire currently used for arch stabilization. Stainless steel, of the type which may be utilized to form the links described herein, is disclosed in an article by D. R. Bearn, entitled "Bonded Orthodontic Retainers: A Review", *Am. J. Orthod. Orthop.*, (1995) No. 108, Pages 207–13. In addition, as another preferred embodiment, the links may be formed of the noble metals and their alloys, particularly gold alloy and platinum.

The arch stabilization device of the present invention can be bonded directly to teeth of a patient, for example, by cementing selected links to selected teeth in the manner set forth in the article by Bearn described above for fixed retainers of orthodontic wire. The device can also be secured to the teeth of a patient by means of mesh bases affixed to selected teeth to which selected links of the device of the present invention are secured to mesh bases.

The device of the present invention thus installed, will maintain the desired longitudinal tension or forces on the arch between the teeth to which the device is secured, while resisting deformation, or more than momentary deformation followed by return to device to its prior position after an angled or transverse force to the device has been encountered.

DESCRIPTION OF THE PREFERRED EMBODIMENTS

Figure 1:
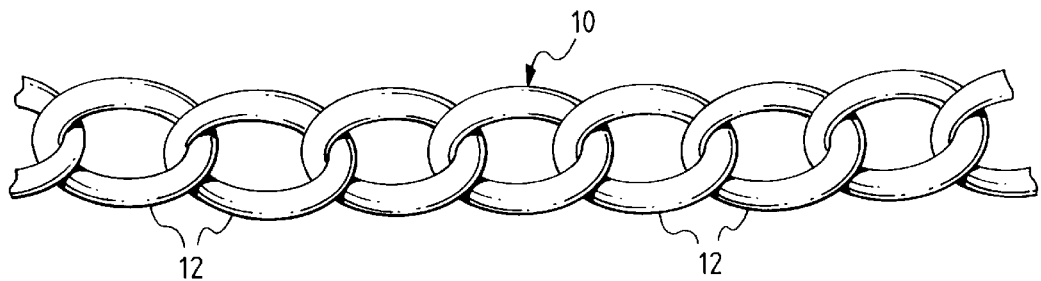
FIG. 1 is an enlarged side elevation of a plurality of links connected to form an arch stabilization device in accordance with the present invention.

In a preferred embodiment of the arch stabilization device of the present invention, which is illustrated in FIG. 1, generally by the reference number 10, a plurality of links 12 are connected in chain-like fashion to form a chain of links 12. The links 12, and hence the device 10, are adapted to be secured to selected teeth 14 (FIGS. 2 and 3) of a patient to be treated. It is preferred that the links 12 are formed to form a relatively flat elongated device 10 by having the links 12 having twisted or flattened portions, to facilitate bonding to selected teeth 14 of the patient and to reduce the thickness of device 10.

Links 12 are preferably rigid, while device 10 is relatively flexible due to its chain-like structure. Also, preferably, links 12 are formed of metal, with stainless steel being one preferred embodiment of metals, which can be used to form links 12. Links 12 also desirably may be formed of alloys of at least two metals. Another preferred embodiment is to form the links of metal selected from the noble metals and their alloys. Particular embodiments of noble metals and their alloys from which links 12 may be formed are gold alloys of the type used by dentists for gold inlays and crowns; and platinum of the type used by orthodontists. Particular types of alloy of at least two metals from which links 12 may be formed are alloys of nickel and titanium; nickel, titanium and copper; copper, zinc and aluminum; copper, zinc, aluminum and manganese; copper, aluminum, nickel and manganese; such as the alloys described for use in multi-strand recovery metal alloys arch wires in U.S. Pat. No. 5,344,315.

Figure 3:
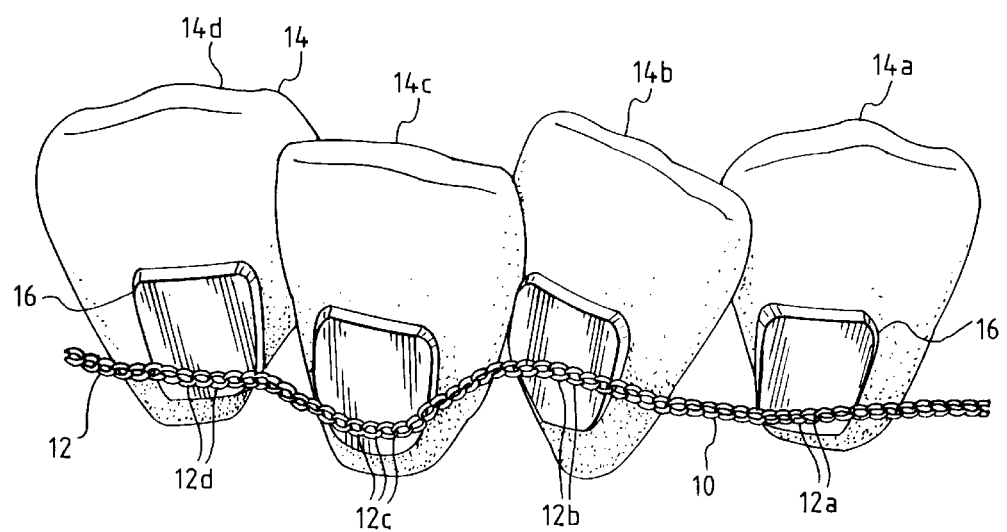
FIG. 3 is a perspective view similar to FIG. 2, in which the arch stabilization device of FIG. 1 is secured directly to a plurality of malaligned teeth.

As illustrated in FIG. 3, device 10 can be positioned to selected teeth 14 of a patient to be treated by securing selected links, such as links 12a, 12b, 12c and 12d directly to selected teeth 14a, 14b, 14c and 14d, respectively. Links 12a–12d can be secured to respective teeth 14a–14d by etching selected surfaces of teeth 14a–14d, and applying a layer or portion 16 of cement or adhesive of the type and material disclosed to the article by Bearn cited above. While layer 16 is still tacky or uncured, device 10 is positioned thereon and partially therein to maintain teeth 14 and/or the arch formed by teeth 14 in position and device 10 held in position while layer 16 dries and hardens or is cured. In the case of orthodontic repositioning of selected teeth of the patient, layer 16 is applied as described, and device 10 positioned on and partially in layer 16 on each selected tooth 14a–14d and held under tension while the layer 16 dries and hardens or is cured to maintain desired longitudinal force between the selected teeth.

Figure 2:
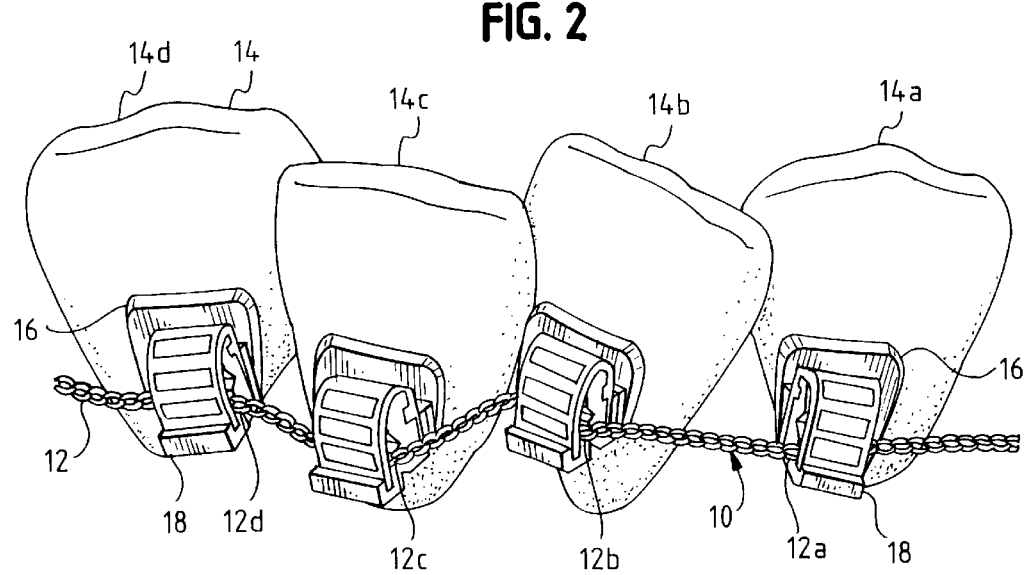
FIG. 2 is a perspective view from the labial and gingival of a plurality of malaligned teeth having brackets secured thereto, and interconnected by the arch stabilization device of FIG. 1.

Another embodiment of the manner of use of device 10 of the present invention employs the use of brackets 18 which supports device 10 on selected teeth 14 of the patient. FIG. 2 illustrates one type of bracket 18 which may be used, although any of the brackets hereto used to support arch devices, such as arch wires can be used as brackets 18. The particular self-ligating bracket shown in the drawing as exemplary, is described in detail in U.S. Pat. No. 5,344,315, which incorporates by reference U.S. Pat. No. 4,492,573. Brackets 18 are secured to selected teeth 14a–14d by means of layers 16 or portions of cement or adhesive as described in the last mentioned embodiment, and after the layers 16 are dried and hardened or cured, device 10 can be placed in the brackets 18 and the brackets 18 closed to lock device 10 in place while maintaining the longitudinal and, if desired, vertically angled, tension between selected teeth to reposition or stabilize the teeth in the arch of the patient.

A particular embodiment of a method of using the orthodontic arch stabilization device of the present invention comprises the following steps:

(a) Polishing or lightly abrading the lingual (tongue) side of the lower incisors and canines of the patient to remove as much of the tartar, stain and plaque as is practical. A preferred method of polishing is to use a "football"shaped burr followed by application of a slurry of pumice or pumice-like material. The polishing step may include removing, for example, by use of the burr mentioned above in a relatively high speed handpiece of a drill, any raised marginal ridges of the lingual surfaces that may interfere with having an even contour of the lingual surfaces of these teeth. Optionally, if desired, the polishing step may include etching the lingual surfaces of each tooth, for example with an etching agent of 30% aqueous solution of phosphoric acid, such as "Liquid Etchant"marketed by Reliance Orthodontic Products, Inc., of Itasca, Ill., for approximately 40–45 seconds, followed by rinsing to remove the etchant, drying with a flow of air, and, optionally, apply to the surfaces a liquid bonding booster or catalyst, such as "Enhance", also marketed by Reliance Orthodontic Products, Inc.

(b) Providing a length of an arch stabilization device of the present invention, preferably etched mechanically or with an acid for better adhesion, measured so as to fit for passive contact to the lingual surfaces of each of the teeth to be stabilized.

(c) Applying a dental adhesive to the middle center of the lingual surfaces of the teeth to be stabilized, for example, by applying a light curable dental adhesive, such as LCR, a mixture primarily of glass frit with minor amounts of amorphous silica and bisphenol diglycidylmethacrylate, or light cured 45% filled resin bond, a mixture of silica, bis-GMA and ethoxylated derivative of bis-GMA, polyethylene glycol dimethacrylate, amine and ketone photoinitiator, both marketed by Reliance Orthodontic Products, Inc. of Itasca, Ill., which is optionally first mixed with a sealer, also marketed by Reliance Orthodontic Products, Inc., to the preferably etched middle center of the lingual surfaces.

(d) placing the selected length of the device of the present invention so that selected links thereof are placed at least partially in the adhesive applied to the lingual surface of each tooth to be stabilized, preferably with a planar portion of the link facing the lingual surface.

(e) at least partially curing the adhesive, preferably with ultraviolet light if a light curable adhesive such as the adhesive in step (c) above, is utilized as the adhesive, for example in the latter case, by applying ultraviolet light for about 30–40 seconds.

(f) optionally applying a top or overcoat layer of adhesive, such as a light curable adhesive, for example the adhesive described in step (c) above, to the links of the device in the areas where the selected links have been placed into contact with the first applied adhesive in the middle center of the lingual surfaces of the teeth to be stabilized, and in contact with the first applied adhesive to bond thereto.

(g) and completely curing the adhesive applied to the lingual surfaces, and the links of the device if adhesive applied thereto; and (h) optionally, polishing and grinding any rough spots of the adhesive so as present a smooth surface of the device and adhesive to the tongue of the patient.

While particular embodiments of the orthodontic arch stabilization device of the present invention has been shown and described, it will be appreciated by those skilled in the art that changes and modifications may be made thereto without departing from the invention in its broader aspects and as set forth in the following claims.

I claim:

1. An orthodontic arch stabilization device adapted to be secured to selected teeth of a patient to be treated, comprising a plurality of links connected to form an elongated chain and adapted to have selected links thereof secured to selected teeth of the patient.

2. The orthodontic arch stabilization device of claim 1, wherein said links are rigid.

3. The orthodontic arch stabilization device of claim 1, wherein said links are formed of metal.

4. The orthodontic arch stabilization device of claim 3, wherein said links are formed of stainless steel.

5. The orthodontic arch stabilization device of claim 3, wherein the metal is selected from the noble metals and their alloys.

6. The orthodontic arch stabilization device of claim 5, wherein the metal is a gold alloy.

7. The orthodontic arch stabilization device of claim 5, wherein the metal is platinum.

8. The orthodontic arch stabilization device of claim 3, wherein said links are formed of an alloy of at least two metals.

9. The orthodontic arch stabilization device of claim 8, wherein the metal is an alloy of nickel and titanium.

10. A method of stabilizing teeth of a patient comprising:

(a) preparing lingual surfaces of teeth to be stabilized to accept an adhesive;

(b) providing an arch stabilization device comprising a plurality of links connected to form an elongated chain and adapted to have selected links thereof secured to the lingual surfaces of the teeth to be stabilized, said arch stabilization device having a length measured to provide passive contact with the lingual surfaces of the teeth to be stabilized;

(c) applying a dental adhesive to the lingual surfaces of the teeth to be stabilized;

(d) placing said arch stabilization device to the adhesive applied to the lingual surfaces of the teeth to be stabilized so that links of the device are in passive contact with the lingual surface of each tooth to be stabilized;

(e) at least partially curing the adhesive applied to the lingual surfaces of the teeth to be stabilized.

11. The method of claim 10, wherein the adhesive applied to the lingual surfaces of the teeth to be stabilized is a light curable adhesive, and said at least partial curing of the adhesive is performed by applying light to said applied adhesive.

12. The method of claim 10, wherein additional dental adhesive is applied to the links of said arch stabilization device in contact with the adhesive first applied to the lingual surfaces of the teeth to be stabilized and to the first applied adhesive therebetween, and completely curing the applied adhesive.

13. The method of claim 12 wherein the adhesive and additional adhesive of said device in contact with the first applied adhesive applied to the lingual surfaces of the teeth to be stabilized and to the links in contact therewith, are at least one light curable adhesive, and wherein the at least partially curing step is performed by applying light to said adhesive.

14. The method of claim 13, wherein the adhesive and additional adhesive are completely cured by applying light thereto.

15. The method of claim 10, wherein the applied adhesive is curable by applying ultraviolet light, and the step of at least partially curing the adhesive applied to the lingual surfaces of teeth to be stabilized is performed by applying ultraviolet light thereto.

16. The method of claim 15, wherein additional dental adhesive which is curable by applying ultraviolet light is applied to the links of said arch stabilization device in contact with the adhesive first applied to the lingual surfaces of the teeth to be stabilized and to the first applied adhesive therebetween, and completely curing the adhesive by applying ultraviolet light thereto.

17. The method of claim 10, wherein the step of preparing lingual surfaces of teeth to be stabilized includes lightly abrading the lingual side surface of the teeth to be stabilized.

18. The method of claim 10, wherein the step of preparing lingual surfaces of teeth to be stabilized includes applying a slurry of pumice thereto.

19. The method of claim 10, wherein the step of preparing lingual surfaces of teeth to be stabilized includes etching the lingual surfaces of each tooth to be stabilized.

* * * * *